United States Patent [19]

Goldsworthy et al.

[11] Patent Number: 4,595,540

[45] Date of Patent: Jun. 17, 1986

[54] BENZONITRILE AND BENZOTHIOCYANO INTERMEDIATES

[75] Inventors: John Goldsworthy, Bracknell, England; Winston S. Marshall, Bargersville, Ind.; John P. Verge, Henley-on-Thames, England

[73] Assignee: Lilly Industries Limited, London, England

[21] Appl. No.: 543,196

[22] Filed: Oct. 19, 1983

[30] Foreign Application Priority Data

Oct. 21, 1982 [GB] United Kingdom ................. 8230076

[51] Int. Cl.$^4$ .................... C07C 121/76; C07C 161/02

[52] U.S. Cl. .................................... 558/414; 578/253; 578/251; 558/413; 558/13

[58] Field of Search ............. 548/253; 260/454, 465 F

[56] References Cited

FOREIGN PATENT DOCUMENTS

| | | | |
|---|---|---|---|
| 0028063 | 5/1981 | European Pat. Off. . | |
| 56172 | 7/1982 | European Pat. Off. . | |
| 83228 | 7/1983 | European Pat. Off. . | |
| 2173778 | 3/1972 | France . | |
| EP80371 | 11/1981 | United Kingdom | 548/253 |

*Primary Examiner*—Glennon H. Hollrah
*Assistant Examiner*—D. B. Springer
*Attorney, Agent, or Firm*—Charles W. Ashbrook; Arthur R. Whale

[57] ABSTRACT

There are described compounds of the formula

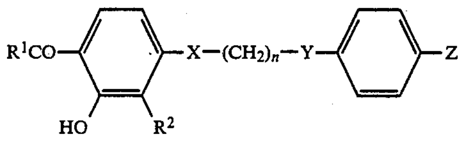

(I)

in which $R^1$ is hydrogen or $C_{1-6}$alkyl, $R^2$ is hydrogen, $C_{1-6}$alkyl or $C_{3-6}$alkenyl, X and Y are each oxygen, sulphur, sulphinyl or sulphonyl, n is 2 to 6 and Z is 1H-tetrazol-5-yl, 1H-tetrazol-5-ylthio, 1H-tetrazol-5-ylsulphinyl, 1H-tetrazol-5-ylsulphonyl, cyano or thiocyano, provided that when both X and Y are oxygen Z is 1H-tetrazol-5-ylthio, 1H-tetrazol-5-ylsulphinyl, 1H-tetrazol-5-ylsulphonyl or thiocyano; and salts thereof. The compounds in which Z is other than cyano or thiocyano have pharmaceutical activity and inhibit leukotriene action or formation.

4 Claims, No Drawings

BENZONITRILE AND BENZOTHIOCYANO INTERMEDIATES'

This invention relates to novel compounds, pharmaceutical compositions containing them and their use as pharmaceuticals.

The compounds of the invention are of the formula (I)

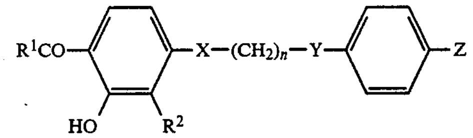

in which $R^1$ is hydrogen or $C_{1-6}$alkyl, $R^2$ is hydrogen, $C_{1-6}$alkyl or $C_{3-6}$aklenyl, X and Y are each oxygen, sulphur, sulphinyl or sulphonyl, n is 2 to 6 and Z is 1H-tetrazol-5-yl, 1H-tetrazol-5-ylthio, 1H-tetrazol-5-ylsulphinyl, 1H-tetrazol-5-ylsulphonyl, cyano or thiocayano, provided that when both X and Y are oxygen Z is 1H-tetrazol-5-ylthio, 1H-tetrazol-5-ylsulphinyl, 1H-tetrazol-5-ylsulphonyl or thiocyano; and salts thereof.

Compounds of the aboce formula (I), with the exception of those in which Z is cyano or thiocyano which are intermediates in the preparation of the remaining compounds, have useful pharmaceutical properties. They are indicated for use inter alia in the prophylactic and thereapeutic treatment of immediate hypersensitivity diseases included asthma and in the alleviation of *status asthmaticus.*

A particular group of compounds according to formula (I) are those in which $R^1$ is hydrogen or $C_{1-6}$alkyl, $R^2$ is hydrogen, $C_{1-6}$alkyl or $C_{3-6}$alkenyl, X and Y are each oxygen or sulphur, n is 2 to 6, and Z is CN or 1H-tetrazol-5-yl, provided that X and Y cannot both be oxygen.

A further group of compounds according to the invention are those of formula (I) in which $R^1$ is hydrogen or $C_{1-6}$alkyl, $R^2$ is hydrogen, $C_{1-6}$alkyl or $C_{3-6}$alkenyl, X and Y are each oxygen, suplur, sulphinyl or sulphonyl, n is 2 to 6 and Z is 1H-tetrazol-5-yl, 1H-tetrazol-5-ylthio, 1H-tetrazol-5-ylsulphinyl, 1H-tetrazol-5-ylsulphonyl, cyano or thiocyano, provided that when X and Y are each oxygen or sulphur, Z is 1H-tetrazol-5-ylthio, 1H-tetrazol-5-ylsulphinyl, 1H-tetrazol-5-ylsulphonyl or thiocyano. Such compounds are preferably those in which X and Y are each oxygen or sulphur and Z is 1H-tetrazol-5-ylthio, 1H-tetrazol-5-ylsulphinyl, 1H-tetrazol-5-ylsulphonyl or thiocyano.

In the above formula (I) reference to a "$C_{1-6}$alkyl" group includes, for exampe, methly, ethyl, propyl, isopropyl and tert. butyl, and a "$C_{3-6}$alkenyl" group includes for example allyl, isopropenyl, butenyl, isobutenyl and 3-methyl-2-butenyl.

In the above formula (I) it is preferred that $R^1$ is $C_{1-6}$alkyl. The preferred value of $R^2$ is $C_{1-6}$alkyl and the preferred values of X are oxygen or sulphur and of Y sulphur. It is moreover preferred that n should be 2 to 4. Thus an especially preferred group of pharmaceutical compounds according to the invention is of formula (I) in which $R^1$ is $C_{1-4}$alkyl, $R^2$ is $C_{1-6}$alkyl, X is oxygen or sulphur, Y is sulphur, n is 2 or 3 And Z is 1H-tetrazol-5-yl or 1H-tetrazol-5-ylthio; and pharmaceutically acceptable salts thereof.

A particularly useful group of pharmaceutical compounds is of the following formula

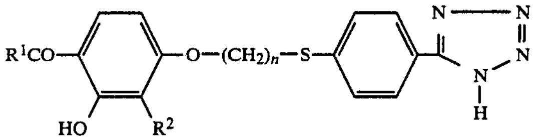

in which $R^1$ is $C_{1-6}$ alkyl, $R^2$ is $C_{1-6}$ alkyl, n is 2 or 3; and pharmaceutically acceptable salts thereof. A further group of especially useful compounds is of the formula

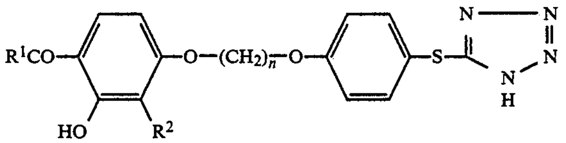

where $R^1$, $R^2$ and n have the above defined meanings; and pharmaceutically acceptable salts thereof.

When the compound of formula (I) bears a tetrazolyl, tetrazolylthio, tetrazolylsulphinyl or tetrazolylsulphonyl group, or the compound has some other acidic substituent, base addition salts can be prepared and these are regarded as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms are particularly preferred.

Apart from pharmacuetically acceptable addition salts, other salts are also included within the scope of the invention such as, for example, those with picric or oxalic acid, since they may serve as intermediates in the purification of compounds or in the preparation of other pharmaceutically acceptable salts, or they may be useful for identification, characterization or purification of the free compound.

The pharmaceutical compounds of the invention can be prepared by a process which comprises reacting a compound of formula (1) in which Z is CN or SCN with an azide, optionally followed when X and/or Y is sulphinyl or sulphonyl or Z is tetrazolylsulphinyl or tetrazolylsulphonyl, by oxidation.

The process of the invention is preferably carried out in an organic solvent such as a polar aprotic solvent for example dimethyl formamide and suitably at a temperature in the range of from 25° C. to 150° C. The azide employed can be, for example, an alkali metal azide and we have found that a combination of alkali metal azide, for example sodium azide, and ammonium chloride is especially convenient.

When it is desired to convert a sulphur atom in the resulting compound to a sulphinyl group:

one of the conventional reagents for such purpose can be employed and a mild oxidising agent such as hydrogen peroxide in methanol or alkali metal periodate in aqueous alcohol is especially convenient, the reaction generally being carried out at a temperature of from 25° C. to the reflux temperature of the reaction mixture. In the case of compounds in which there is a sulphonyl group:

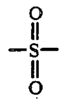

a stronger oxidising agent must be employed such as for example hydrogen peroxide in acetic acid or meta-chloroperbenzoic acid in methanol, the reaction being performed at a temperature of from 25° C. to 100° C.

Compounds of formula (I) in which Z is CN or SCN can be prepared by condensing a compound of formula (II)

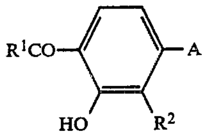

with a compound of formula (III)

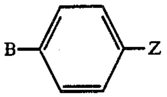

in which $R^1$ and $R^2$ have the values defined above, Z is CN or SCN, and one of A and B is OH or SH and the other is $-X(CH_2)_nX'$, where X' is a leaving group. Thus, for example, the cyano and thiocyano intermediate compounds in which X is oxygen and Y is sulphur can for example be prepared according to the following reaction

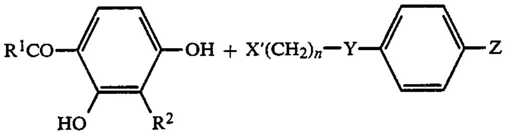

(IV) (V)

where $R^1$, $R^2$ and n have their above defined meanings, Z is CN or SCN and X' is a leaving group such as, for example, halogen especially bromine or chlorine. Such a reaction can be carried out in an inert organic solvent in the presence of a base such as for example sodium hydride in dimethyl formamide or anhydrous sodium carbonate and methyl ethyl ketone, and preferably at an elevated temperature such as for example from 50° C. to the reflux temperature.

Compounds of formula (IV) are known compounds or can be prepared from known compounds by methods well-known in the art. Compounds of formula (V) can be prepared, for example, from 4-cyanophenol by a series of reactions involving first the preparation of 4-mercaptobenzonitrile by reaction of the phenol with dialkylthiocarbamoyl halide to give the 0-substituted-N,N-diethylthiocarbamate which on heating with zinc rearranges to provide the corresponding S-substituted compound. Treatment with base at elevated temperatures gives the 4-mercaptobenzonitrile. The sequence of reactions can be illustrated for the preparation of 4-mercaptobenzonitrile as follows:

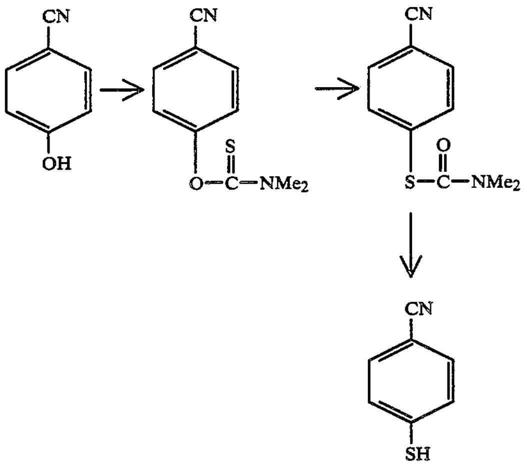

The resulting 4-mercapto-benzonitrile can then be reacted with the appropriate reagent of formula $X'(CH_2)_nX''$ where X'' is a leaving group such as for example a halogen atom, as follows:

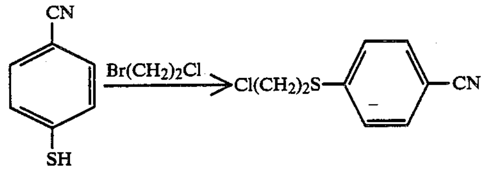

When it is desired to prepare cyano or thiocyano intermediate compounds in which X and Y in formula (I) are both oxygen or sulphur, or in which X is sulphur and Y is oxygen, similar preparative techniques may be employed to those described above.

The compounds of the present invention are pharmacologically active, being inhibitors of leukotriene action as shown by the following tests: (a) the in vitro test on guinea pig ileum segments at concentrations of from 10 ng to 50 μg, according to the method of Schild, 1947 Brit. J. Pharm. 2,197-206 (the pharmacological compounds of the following Examples exhibited an $IC_{50}$ against LTD4 of less than $10^{-4}$ molar); (b) the in vivo Guinea Pig Pulmonary Function Test of Austen and Drazen 1974 J. Clin. Invest. 53:1679-1685 at intravenous dosage levels of from 0.05 μg to 5.0 mg/kg; and (c) a modified "Herxheimer" test at doses of from 25 to 200 mg/kg. The "Herxheimer" test is based on an allergic bronchospasm induced in guinea pigs and which closely resembles an asthmatic attack in man. The mediators causing the bronchospasm are very similar to those released when sensitised human lung tissue is challenged with an antigen. In the modified test employed in respect of compounds of the present invention, the animals were pretreated with a histamine antagonist, mepyramine, at a dose of 0.5 mg/kg i.p., 30 minutes before challenge. This modification masks the histamine effect to reveal better the leukotriene effect. The compounds also inhibit the formation of leukotrienes as indicated by their action in the test described by Harvey and Osborne Journal of Pharmacological Methods 9, 147-155 (1983).

The compounds are accordingly indicated for therapeutic use in the treatment of diseases in which leukotrienes are implicated. These include immediate hypersensitivity diseases, allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever.

The compounds may be administered by various routes, for example, by the oral or rectal route, by inhalation, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, and/or enclosed within a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols as a solid or in a liquid medium, ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, more usually 25 to 200 mg, of the active ingredient. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and for example dosages per day will normally fall within the range of 0.5 to 300 mg/kg. and in the treatment of adult humans, more usually in the range of from 5 to 100 mg/kg. However it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention.

EXAMPLE 1

(i) 0-(4-Cyanophenyl)-N,N-dimethylthiocarbamate

A mixture of 4-cyanophenol (59.5 g) potassium carbonate (75.9 g), dimethylthiocarbamoyl chloride (72.9 g) and dry acetone (1 liter) was stirred at room temperature for two hours, then refluxed for 16 hours (see Newman and Karnes J.O.C. 31 3980 (1966)).

The reaction mixture was cooled, poured into water (3 liters) and stirred vigorously for 30 minutes. The solid material was collected by filtration, washed with water on the sinter, and dried in vacuo to give the product as an off white solid, melting point 122°-123° C.

(ii) S-(4-Cyanophenyl)-N,N-dimethylthiocarbamate

The product from (i) (51.0 g) was heated with zinc wool (4.0 g) under a nitrogen stream at 220° C. for 3 hours.

The crude product was recrystallised ($CCl_4$/hexane) to give pure white needles, melting point 110° C.

(iii) 4-Mercaptobenzonitrile

The product from (ii) (35.3 g) was refluxed with a 4% ethanolic potassium hydroxide solution (720 ml) for two hours.

The ethanol was evaporated off, the residue suspended in water and acidified with 2 molar hydrochloric acid. The resulting precipitate was collected by filtration and dried to give the title compound as a yellowish solid, melting point about 60° C.

(iv) 3-(4-Cyanophenylthio)-1-chloropropane

To a refluxing suspension of 4-mercaptobenzonitrile (10.00 g), potassium carbonate (30.67 g) and dry acetone (100 ml) was added 1-bromo-3-chloropropane (11.67 g) and refluxing was continued for further three hours. At this stage an additional amount (6 g) of bromochloropropane was added, then refluxing was continued for a further 16 hours.

The reaction mixture was evaporated in vacuo, the residue stirred with water (100 ml), then extracted with dichloromethane (2×100 ml); the extracts were dried and evaporated to give a yellow oil. The crude oil was distilled on a Vigreux column and the fraction of boiling point 160° C/0.4 mmHg collected to yield the product as a colourless oil, which crystallised on standing.

(v) 4-[3-(4-Acetyl-3-hydroxy-2-propylohenoxy)propylthio]-benzonitrile.

To a suspension of benzene-washed 50% sodium hydride (0.57 g) in dry dimethylformamide (50 ml) was added 2,4-dihydroxy-3-propyl-acetophenone (4.56 g) and sodium iodide (3.55 g), and the mixture stirred at 50° C. for 20 minutes. A solution of 3-(4-cyanophenylthio)-1-chloropropane (5.00 g) in dry dimethylformamide (15 ml) was then added dropwise, and the reaction mixture heated and stirred at 100° C. for four hours.

The reaction mixture was cooled, the dimethylformamide evaporated in vacuo, the residue stirred with water (100 ml) and extracted with dichloromethane (2×100 ml). The combined extracts were washed with 25% sodium carbonate solution (2×150 ml) and water (2×200 ml), dried ($MgSO_4$) and evaporated to give the product as a brown oil which rapidly crystallised, melting point 100° C.

(vi) 1-{2-Hydroxy-3-propyl-4-[3-(4-(1H-tetrazol-5-yl) phenylthio)propoxy]phenyl}ethanone.

To a solution of the benzonitrile (prepared as in (v) above) (6.7 g) in dry dimethylformamide (60 ml) was added sodium azide (2.96 g) and ammonium chloride (2.44 g) and the suspension was heated at 120° C. for two hours. A further amount cf sodium azide (1.2 g) and ammonium chloride (1.0 g) was then added and heating was continued for a further two hours.

The reaction mixture was cooled, stirred with water (600 ml), and the filtered material dried in vacuo and finally recrystallised from ethanol/water (with charcoal decolourisation) to give the title compound as a beige solid, melting point 160°-162° C.

The following compounds were prepared in a similar manner

4-[2-(4-Acetyl-3-hydroxy-2-propylphenoxy)ethylthio]-benzonitrile, melting point 114°-116° C.

1-{2-Hydroxy-3-propyl-4-[2-(4-(1H-tetrazol-5-yl)phenylthio)ethoxy]phenyl}ethanone, melting point 167°-169° C.

EXAMPLE 2

(i) 2-Hydroxy-3-propyl-4-thioacetophenone

The above compound was prepared as described in Example 1 following the steps (i), (ii) and (iii) using 2,4-hydroxy-3-propylacetophenone as starting material, melting point 70°-72° C.

(ii)

2-Hydroxy-3-propyl-4-(3-chloropropylthio)acetophenone.

The above compound was prepared as described in Example 1 (iv) using the product of (i) above. The resulting compound was a liquid, boiling point 205° C./0.05 mm mercury.

(iii)

4-[3-(4-Acetyl-3-hydroxy-2-propylphenylthio)propoxy]-benzonitrile

This compound was prepared as described in Example 1(v) using 4-cyanophenol and the product of (ii) above, melting point 90°-92° C.

(iv)

1-{2-Hydroxy-3-propyl-4-[3-(4-(1H-tetrazol-5-yl)phenoxy)propylthio]phenyl}ethanone.

This compound was prepared as described in Example 1(vi) using the benzonitrile of (iii) above as substrate, melting point 178°-182° C.

The following compounds were prepared in a similar manner 4-[2-(4-Acetyl-3-hydroxy-2-propylphenylthio)ethoxy]benzonitrile, melting point 102°-104° C. 1-{2-Hydroxy-3-propyl-4-[2-(4-(1H-tetrazol-5-yl)phenoxy)ethylthio]phenyl}ethanone, melting point 172°-175° C.

EXAMPLE 3

(i)

4-[3-(4-Acetyl-3-hydroxy-2-propylphenylthio)propylthiobenzonitrile

This compound was prepared by the method of Example 1(v) but using 2-hydroxy-3-propyl-4-thioacetophenone, melting point about 80° C.

(ii)

1-{2-Hydroxy-3propyl-4-[3-(4-(1H-tetrazol-5-yl)phenylthio)propylthio]phenyl}ethanone This compound was prepared by the method of Example 1(vi) using the benzonitrile from (i) above as substrate, melting point 160°-162° C.

EXAMPLE 4

1-{2-Hydroxy-3-propyl-4-[3-(4-(1H-tetrazol-5-yl)phenylsulphinyl)propoxy]phenyl}ethanone 1-{2-Hydroxy-3-propyl-4-[3-(4-(1H-tetrazol-5-yl)phenylthio) propoxy]phenyl}ethanone (0.412 g) was dissolved in methanol (20 ml) and 20% aqueous hydrogen peroxide (0.7 ml) added. The resulting solution was refluxed for 36 hours (see Drabowicz and Mikozajczyk Synth. Comm. 11 (12) 1025 to 1030 (1981)).

Water (20 ml) was added, the methanol evaporated in vacuo, the remaining aqueous phase extracted with ethyl acetate (2×20 ml); the combined organic extracts were dried with magnesium sulphate and evaporated in vacuo to give a pale yellow solid which was recrystallised from ethanol/water (with decolourising charcoal) to give the product sulphoxide as fluffy white crystals, melting point 130° C., with decomposition.

The following compound was prepared in a similar manner

1-{2-Hydroxy-3-propyl-4-[2-(4-(1H-tetrazol-5-yl)phenylsulphinyl)ethoxy]phenyl}ethanone, melting point 128°-130° C.

EXAMPLE 5

1-{2-Hydroxy-3-propyl-4-[3-(4-(1H-tetrazol-5-yl)phenylsulphonyl)propoxy]phenyl}ethanone.

1-{2-Hydroxy-3-propyl-4-[3-(4-(1H-tetrazol-5-yl)phenylthiopropoxy]pheny}ethanone (0.412 g) was dissolved in glacial acetic acid (6 ml) and 20% aqueous hydrogen peroxide (1 ml) was added to the mixture. The resulting solution was heated at 60° C for 24 hours.

The reaction mixture was cooled, poured into water (75 ml) and stirred vigorously for 30 minutes. The flocculent precipitate was collected by filtration, dried in vacuo and finally recrystallised from ethanol/water (with decolourising charcoal) to give the required sulphone as a white solid, melting point 120° C.

The following compounds were prepared in a similar manner

1-{2-Hydroxy-3-propyl-4-[3-(4-(1H-tetrazol-5-yl)phenoxy)propylsulphonyl]phenyl}ethanone, melting point 168°-172° C.

1-{2-Hydroxy-3-propyl-4-[2-(4-(1H-tetrazol-5-yl)phenylsulphonyl)ethoxy]phenyl}ethanone, melting point 197°-199° C.

EXAMPLE 6

1-{2-Hydroxy-3-propyl-4-[3-(4-thiocyanophenoxy)-propoxy]phenyl}ethanone

A mixture of 4(3-chloropropoxy)-2-hydroxy-3-propylacetophenone (4.06 g) 4-thiocyanophenol (JACS Vol. 78 p 858) (2.25 g), sodium iodide (2.25 g), and anhydrous sodium carbonate (6 g) was boiled and stirred under reflux in methyl ethyl ketone (60 ml, anhydrous) for 80 hours. The solvent was evaporated and the residual mass stirred with water (100 ml) and dichloromethane (100 ml). The organic layer was separated and the aqueous layer extracted a second time with dichloromethane (100 ml). The two organic layers were combined, washed with water and dried over anhydrous magnesium sulphate. After evaporation there remained 5.0 g of a yellow gum which slowly crystallized. This was recrystallized from ether/light petrol ether to give 3.2 g white solid, melting point 85° C.

The following compound was similarly prepared 1-{2-Hydroxy-3-propyl-4-[2-(4-thiocyanophenoxy)ethoxy]phenyl}ethanone, melting point 86° C.

EXAMPLE 7

1-{2-Hydroxy-3-propyl-4-[3-(4-(1H-tetrazol-5-ylthio)-phenoxy)propoxy]lphenyl}ethanone A mixture of 1-{2-hydroxy-3-propyl-4-[3-(4-thiocyanophenoxy)propoxy]phenyl}ethanone (7.7 g), sodium azide (3.9 g) and ammonium chloride (3.2 g) dissolved in anhydrous dimethylformamide (40 ml) was stirred and heated at 115° C. for 4 hours.

The mixture was poured into 200 ml ice/water and the pH adjusted to 3.0 with N hydrochloric acid, resulting in a yellow precipitate. This was collected, washed with water, and dissolved in 2N NaOH solution (80 ml). This solution was extracted twice with 40 ml ether and the organic layers discarded. The aqueous layer was acidified with 5N hydrochloric acid, resulting in a sticky solid precipitate. After crystallization from aqueous methanol there was obtained 5.9 g of a pale yellow solid, melting point 114° C.

The following compound was similarly prepared. 1-{2-Hydroxy-3-propyl-4-[2-(4-(1H-tetrazol-5-ylthio)-phenoxy)ethoxy]phenyl}ethanone, melting point 160° C.

EXAMPLE 8

1-{2-Hydroxy-3-propyl-4-[2(1H-tetrazol-5-ylsulphonyl)phenoxy)ethoxy]phenyl}ethanone 1-{2-Hydroxy-3-propyl-4-[2-(4-(1H-tetrazol-5-ylthio)phenoxy)ethoxy]phenyl}ethanone (1.85 g), was dissolved in 30 ml glacial acetic acid. Hydrogen peroxide (100 vol, 5 ml) was added and the mixture stirred and heated at 70° C. for 6 hours. The solvent was evaporated off under vacuum and the residue triturated with water to give a solid. After recrystallization from ether/light petroleum there was obtained 1.02 g of white product, melting point 100°-102° C.

The following compound was similarly prepared 1-{2-Hydroxy-3-propyl-4-[3-(4-(1H-tetrazol-5-ylsulphonyl phenoxy)propoxy]phenyl}ethanone, melting point 88°-90° C.

The following formulations are prepared from pharmaceutical compounds according to the invention as described in the above Examples

EXAMPLE 9

| Aerosol | |
|---|---|
| Active Ingredient | 100 mg |
| Ethanol | 30 ml |
| Propellent 12/114 | q.s. |

The active ingredient is dissolved in ethanol, filled into glass bottles, sealed with a valve (metered to 0.05 ml) and charged with the mixed propellants.

EXAMPLE 10

| Tablet | |
|---|---|
| Active ingredient | 100 mg |
| Dried starch | 400 mg |
| Polyvinyl pyrrolidone | 50 mg |
| Sodium carboxymethyl starch | 50 mg |
| Stearic acid | 20 mg |

The active ingredient and starch are mixed together and massed with a solution of polyvinyl pyrrolidone in alcohol. The mass is extruded through a screen, dried, sized and mixed with sodium carboxymethyl starch and stearic acid prior to compression on a tablet machine. Tablets weighing 620 mg are obtained.

EXAMPLE 11

| Capsules | |
|---|---|
| Active ingredient | 50 mg |
| Starch flowable | 300 mg |
| Silicone fluid | 5 mg |

A portion of the starch is mixed with the silicone fluid. To the powder is added the active ingredient and the remainder of the starch. This blended mixture is filled into hard gelatin capsules.

What we claim is:

1. A compound of the formula

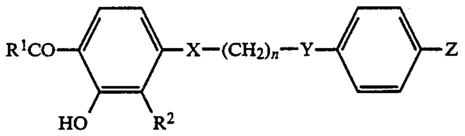

in which $R^1$ is hydrogen or $C_{1-6}$ alkyl, $R^2$ is hydrogen, $C_{1-6}$ alkyl or $C_{3-6}$ alkenyl, X and Y are each oxygen, sulphur, sulphinyl or sulphonyl, n is 2 to 6 and z is cyano or thiocyano provided that when X and Y are oxygen z is thiocyano.

2. A compound according to claim 1 in which $R^1$ is $C_{1-6}$ alkyl, $R^2$ is $C_{1-6}$ alkyl, X is oxygen or sulphur, Y is sulphur, and n is 2 or 3.

3. A compound according to claim 2 in which $R^1$ is $C_{1-6}$ alkyl, $R^2$ is $C_{1-6}$ alkyl, X is oxygen, Y is sulphur, and n is 2 or 3.

4. The compound of claim 3 which is 4-[3-(4-acetyl-3-hydroxy-2-propylphenoxy)propylthio]benzonitrile.

* * * * *